US007354714B2

(12) United States Patent
Gissmann et al.

(10) Patent No.: US 7,354,714 B2
(45) Date of Patent: Apr. 8, 2008

(54) PRODUCTION AND APPLICATIONS FOR POLYVALENT VACCINES AGAINST DISEASES CAUSED BY PAPILLOMA VIRUSES

(75) Inventors: Lutz Gissmann, Wiesloch (DE); Kai Pohlmeyer, Fitzbek (DE); Martin Müller, Neckargernund (DE)

(73) Assignee: Deutsches Krebsforschungszentrum Stiftung des Öffentlichen Rechts, Heidelberg (DE)

( * ) Notice: Subject to any disclaimer, the term of this patent is extended or adjusted under 35 U.S.C. 154(b) by 489 days.

(21) Appl. No.: 10/778,936

(22) Filed: Feb. 13, 2004

(65) Prior Publication Data

US 2005/0026257 A1    Feb. 3, 2005

Related U.S. Application Data

(63) Continuation-in-part of application No. 10/485,454, filed as application No. PCT/EP02/08360 on Jul. 26, 2002.

(30) Foreign Application Priority Data

Jul. 30, 2001  (DE)  .................. 101 37 102

(51) Int. Cl.
   *C12Q 1/68*   (2006.01)

(52) U.S. Cl. .......................... 435/6; 435/69.1

(58) Field of Classification Search .................... 435/6, 435/69.1, 345
See application file for complete search history.

(56) References Cited

U.S. PATENT DOCUMENTS

| | | | |
|---|---|---|---|
| 4,551,270 A | 11/1985 | Danos et al. | |
| 5,045,447 A | * 9/1991 | Minson | ........................ 435/5 |
| 5,626,877 A | 5/1997 | Amsden et al. | |
| 5,820,870 A | 10/1998 | Joyce et al. | |
| 5,821,087 A | 10/1998 | Lowe et al. | |
| 5,840,306 A | 11/1998 | Hofmann et al. | |
| 5,866,553 A | 2/1999 | Donnelly et al. | |
| 5,888,516 A | 3/1999 | Jansen et al. | |
| 5,891,108 A | 4/1999 | Leone et al. | |
| 5,972,027 A | 10/1999 | Johnson | |
| 5,981,173 A | 11/1999 | Orth et al. | |
| 6,025,163 A | 2/2000 | Shamanin et al. | |
| 6,041,252 A | 3/2000 | Walker et al. | |
| 6,066,324 A | 5/2000 | Gissmann et al. | |
| 6,071,305 A | 6/2000 | Brown et al. | |
| 6,074,673 A | 6/2000 | Guillen | |
| 6,083,996 A | 7/2000 | Buyuktimkin et al. | |
| 6,086,582 A | 7/2000 | Altman et al. | |
| 6,086,912 A | 7/2000 | Gilman | |
| 6,110,498 A | 8/2000 | Rudnic et al. | |
| 6,126,919 A | 10/2000 | Stefely et al. | |
| 6,132,765 A | 10/2000 | DiCosmo et al. | |
| 6,136,295 A | 10/2000 | Edwards et al. | |
| 6,142,939 A | 11/2000 | Eppstein et al. | |
| 6,183,745 B1 | 2/2001 | Tindle et al. | |
| 6,221,577 B1 | 4/2001 | Muller et al. | |
| 6,235,312 B1 | 5/2001 | Hobbs et al. | |
| 6,235,313 B1 | 5/2001 | Mathiowitz et al. | |
| 6,245,349 B1 | 6/2001 | Yiv et al. | |
| 6,245,568 B1 | 6/2001 | Volkin et al. | |
| 6,251,079 B1 | 6/2001 | Gambale et al. | |
| 6,251,678 B1 | 6/2001 | Volkin et al. | |
| 6,283,947 B1 | 9/2001 | Mirzaee | |
| 6,283,949 B1 | 9/2001 | Roorda | |
| 6,287,792 B1 | 9/2001 | Pardridge et al. | |
| 6,296,621 B1 | 10/2001 | Masuda et al. | |
| 6,296,832 B1 | 10/2001 | Ruoslahti et al. | |
| 6,309,370 B1 | 10/2001 | Haim et al. | |
| 6,309,375 B1 | 10/2001 | Glines et al. | |
| 6,309,380 B1 | 10/2001 | Larson et al. | |
| 6,309,410 B1 | 10/2001 | Kuzma et al. | |
| 6,317,629 B1 | 11/2001 | Haak et al. | |
| 6,346,272 B1 | 2/2002 | Viegas et al. | |
| 6,350,780 B1 | 2/2002 | Garst et al. | |

(Continued)

FOREIGN PATENT DOCUMENTS

DE    199 25 199    12/2000

(Continued)

OTHER PUBLICATIONS

Beitburd et al., "Human papillomavirus vaccines," *Cancer Biology*, vol. 9, pp. 431-445 (1999).

(Continued)

*Primary Examiner*—Ali R. Salimi
(74) *Attorney, Agent, or Firm*—Patterson, Thuente, Skaar & Christensen, P.A.

(57) ABSTRACT

A vaccine against disease caused by papilloma viruses is described in certain embodiments, as well as certain vectors, obtainable by the following methods: (a) one or more expression vectors that contain the DNA code for a structural protein of papilloma viruses or a fragment thereof are injected into mammals, whereby in at least some of the expression vectors randomly generated heterologous sequences are inserted into the DNA code (b) serums are obtained from the mammals and these are tested for the presence of antibodies against particles of various papilloma virus types, and (c) using the serums tested, the structural protein gene clones are identified that code for a polyvalent vaccine, and (d) the vaccine is produced from them. Procedures for producing a vaccine is also described, together with its use for vaccination against diseases caused by papilloma viruses.

7 Claims, 4 Drawing Sheets

U.S. PATENT DOCUMENTS

| | | |
|---|---|---|
| 6,358,744 B1 | 3/2002 | Volkin et al. |
| 6,379,382 B1 | 4/2002 | Yang |
| 6,387,124 B1 | 5/2002 | Buscemi et al. |
| 6,387,397 B1 | 5/2002 | Chen et al. |
| 6,649,167 B2 | 11/2003 | Hallek et al. |

FOREIGN PATENT DOCUMENTS

| | | |
|---|---|---|
| DE | 100 59 631 | 7/2002 |
| WO | WO 93/02184 | 2/1993 |
| WO | WO 95/31532 | 11/1995 |
| WO | WO 98/44944 | 10/1998 |
| WO | WO 00/35479 | 6/2000 |
| WO | WO 00/45841 | 8/2000 |
| WO | WO 01/14416 | 3/2001 |
| WO | WO 01/97840 | 12/2001 |
| WO | WO 03/078455 | 9/2003 |

OTHER PUBLICATIONS

Chen et al., "Structure of Small virus-like Particles Assembled fromt heL1 Protein of Human Papillomavirus 16", *Mol. Cell* 5:, 557-567 (2000).

Donnelly et al., "Protection against Papillomavirus with a Polynucleotide Vaccine," *Journal of Infectious Diseases*, vol. 713, pp. 314-320 (1996).

Cole et al., "Nucleotide Sequence And Comparative Analysis Of The Human Papillomavirus Type 18 Genome—Phylogeny Of Papillomaviruses and Repeated Structure of the E6 and E7 Gene Products", *J. Mol. Bio.*, (4); 599-608 (1987).

Giroglou et al., "Immunological analyses of human papillomavirus capsids," *Vaccine*, vol. 19, pp. 1783-1793 (2001).

Kennedy et al., "A Negative Regulatory Element in the human Papillomavirus type 16 Genome Acts at the Level of Late mRNA Stability", *J. Virol.* 65(4), 2093-2097 (1991).

Kotecha et al., "Enhanced tumour growth after DNA Vaccination against Human Papilloma Virus E7 On Coprotein: Evidence for Tumor-Inducted Immune Deviation" *Vaccine* 2003 21 (19-20): 2506-15.

Kowalczyk et al., "Vaccine regimen for prevention of sexually transmitted infections with human papillomavirus type 16," *Vaccine*, vol. 19, pp. 3583-3590 (2001).

Leder et al., "Enhancement of Capsid Gene Expression: Preparing the Human Papillomavirus Type 16 Major Structural Gene L1 for DNA Vaccination Purposes," *J. Virol.*, vol. 75, No. 19, pp. 9201-9209 (Oct. 2001).

Longuet et al., "Two Novel Genital Human Papillomavirus (HPV) Types, HPV68 and HPV70, Related to the Potentially Oncogenic HPV39", *J. Clin. Microbiol.* 34 (3), 738-744 (1996).

Pastrana et al., "NHPV16 VLP Vaccine Induces Human Antibodies That Neutralize Divergent Variants of HPV16," *Virology*, vol. 279, pp. 361-369 (2001).

Pumpens et al. "Evaluation of HBs, and frCP Virus-Like Particles for Expression of Human Papillomavirus 16 E7 Oncoprotein Epitopes" *Intervirology.* 2002, 45(1): 24-32.

Roden et al., "Minor Capsid Protein of Human Genital Papillomaviruses Contains Subdominant, Cross-Neutralizing Epitopes," *Virology*, vol. 270, pp. 254-257 (2000).

Rudolf et al. "Induction of HPV16 Capsid Protein-Specific Human T Cell Responses by Virus-Like Particles" *Biol. Chem.* 1999, 380: 335-40.

Schreckenberger et al., "Induction of an HPV 6bL1-specific mucosal IgA response by DNA immunization," *Vaccine*, vol. 19, pp. 227-233 (2001).

Sundaram et al., "Intracutaneous vaccination of rabbits with the cottontail rabbit papillomavirus (CRPV) L1 gene protects against virus challenge," *Vaccine*, vol. 15, No. 6/7, pp. 664-671 (1997).

Touze et al., "The L1 Major Capsid Protein of Human Papillomavirus Type 16 Variants Affects Yield of Virus-Like Particles Produced in an Insect Cell Expression System," *J. Clin. Microbiol.*, vol. 36, No. 7, pp. 2046-2051 (Jul. 1998).

Xu et al., "Identification of a Novel Mechanism for endotoxin-mediated Down-Modulation of CC Chemokine Receptor Expression" *Eur. J. Immunol.* 2000, 30: 228-9.

Chen et al., "Structure of Small Virus-like Particles Assembled from the L1 Protein of Human Papillomavirus 16", *Molecular Cell*, vol. 5, pp. 557-567, Mar. 2000.

* cited by examiner

PRODUCTION AND APPLICATIONS FOR POLYVALENT VACCINES AGAINST DISEASES CAUSED BY PAPILLOMA VIRUSES

CROSS REFERENCE TO RELATED APPLICATIONS

This application is a Continuation-in-Part of U.S. patent application Ser. No. 10/485,454, filed Jan. 30, 2004, entitled "Polyvalent Vaccine Against Diseases Caused By Papilloma Viruses, Method For The Production And The Use Thereof" which is a U.S. national stage application filed under 35 U.S.C. § 371 and claims priority to PCT/EP02/08360 (WO 03/011335), internationally filed Jul. 26, 2002, which claims priority to DE 101 37 102.0, filed Jul. 30, 2001, priority to all of which are claimed and which are hereby incorporated by reference herein.

FIELD OF USE

Some aspects of certain embodiments of the invention relate to polyvalent antibodies or vaccines against diseases caused by papilloma viruses, as well as the production process and application of the antibodies or vaccines.

BACKGROUND

Papilloma viruses are a family with considerably more than 80 genotypes. Infection with papilloma viruses can lead to warts, papillomas, acanthomas, and skin and cervical carcinomas. A single illness can be caused by various papilloma virus types.

The capsids of the individual types of human pathogenic papilloma viruses (HPV) differ in their antigen characteristics (epitopes), meaning that after immunization with a specific HPV type, neutralizing antibodies cannot be induced against capsids of other HPV types. However, such antibodies would be necessary to give comprehensive protection against diseases that can be caused by different HPV types.

An example is that infection with one of more than ten different HPV types can lead to cervical cancer. Although the virus particles of the individual types are very similar in their composition, they carry different neutralizing epitopes on their surface and are therefore only recognized by the immune system if there has been either a previous natural infection or vaccination with particles of the same type, and type-specific (neutralizing) antibodies are induced.

Vaccines for the effective prevention of diseases caused by HPV should therefore contain a mixture of various virus types in order to give comprehensive protection. The production of such vaccines is, however, rendered more difficult owing to the fact described above, namely that one and the same disease can be caused by different HPV types.

To date only monovalent HPV vaccines have been developed, in other words vaccines directed against only one HPV type. However these have the serious disadvantage that they only guarantee protection against this one special HPV type, and not against other HPV types. Thus, monovalent HPV vaccines do not furnish a comprehensive immune reaction. Moreover, the production of conventional vaccines against HPV typically requires the production and purification of L1.

SUMMARY

Consequently the present invention is based on making a vaccine and also a process for its simple production available with which an immune response against different HPV types can be obtained. By constructing libraries of one type of HPV antigenic biomolecule in which random peptide sequences are inserted, the resulting proteins of some of the clones in the libraries are able to induce neutralizing antibodies against at least two HPV types (e.g., HPV 16, 18, 31, and 45).

The screening of a library of such clones, however, is challenging using conventional techniques. Conventional techniques for screening such a library would involve a step of production and purification of L1. This step, however, may be eliminated by using DNA immunization. Further, many clones may be simultaneously screened by examining sera from an animal that has been inoculated with a plurality of DNA clones.

DETAILED DESCRIPTION

Figure 1:
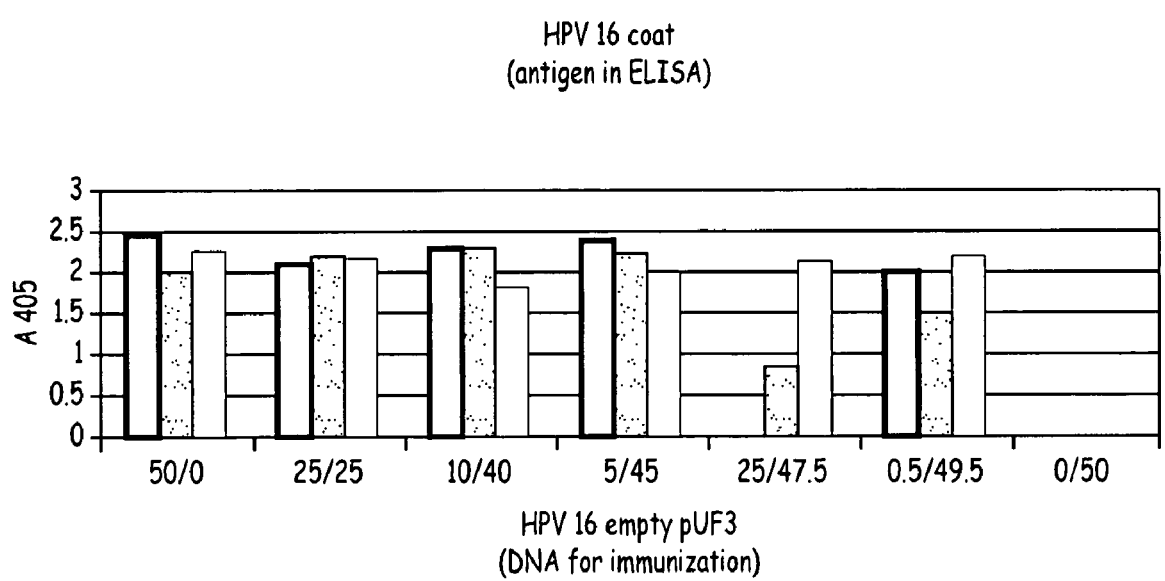
FIG. 1 is a plot of experimental data wherein mice (three per group) were immunized with different amount ratios of HPV 16 L1 DNA and empty pUF3 vector. The sera of the mice were tested in VLP-based ELISA for the presence of anti-HPV 16 antibodies.

By constructing libraries of one type of HPV antigenic biomolecule (e.g., HPV 16 L1) in which random peptide sequences are inserted into surface loops, the resulting proteins of some of the clones in the libraries are able to induce neutralizing antibodies against more than one HPV type (e.g., both HPV 16 and HPV 18).

The antibodies are useful as diagnostic agents for identification of PV, as research reagents, and as markers. For example, antibodies that are generic to PV or to a subset of HPVs may be used to identify PV or a subtype of PV. Scientists commonly use antibodies as tools to identify, inhibit, or label molecules, and a large market for such research tools exists.

DNA clones that elicit an immunogenic response in an animal, e.g., production of an antibody, may be used directly in an animal as a vaccine. Moreover, such clones may be used as research tools. For example, a DNA fragment that encodes an antigen for a plurality of HPVs would be useful for generating antibodies that recognize a plurality of HPVs. And such clones could be used to infect test cells or animals to create a condition wherein they expressed multiple HPV antigens.

A library derived from an HPV antigenic biomolecule (e.g., HPV 16 L1) in which random peptide sequences are inserted into surface loops is useful for screening for antigens that are used to create antibodies against HPV, HPV types (e.g., HPV 16 or HPV 18), and against multiple types of HPV (e.g., both HPV 16 and HPV 18). Alternatively, other types of HPV may be used instead of HPV 16, as will be evident to a person of ordinary skill after reading this disclosure. One specific region of a surface loop of the L1 protein is described below. In general, surface loop regions can be estimated from protein computational algorithms. However, a person of ordinary skill in the art can find surface loop regions based on information in the literature, computational estimates of protein structure and/or empirical evaluation of the resulting antibodies using the approaches described herein using routine experimentation.

A library may be referred to as having members that are clones. Clones are members of a library that have common structural features, but differ from each other with regards to some structural feature. Clones, for example, may be expression vectors having an expression cassette that each encodes a different DNA sequence. It is recognized that some methods of preparing a library may result in some duplicate clones. Nonetheless, since each clone is considered to be distinct from the other, a plurality of clones refers to two clones that are non-identical.

Vaccines and antibodies against a particular type of PV or HPV have been reported, for example, in WO 03078455A3 WO 0045841, WO 0114416A3, WO 9844944, WO 9531532 WO 9302184, U.S. Pat. Nos. 6,649,167 6,358,744, 6,251, 678, 6,245,568, 6,221,577, 6,183,745, 6,066,324, 6,025,163, 5,888,516, 5,866,553, 5,840,306, 5,821,087, and 5,820,870 all of which are hereby incorporated herein by reference. Further, sequence data information and identities for various PVs and HPVs are available in public databases accessible to persons of ordinary skill in these arts; for example U.S. Pat. No. 5,981,173 sets forth sequence data for HPV L1, L2, E6, and E7, NCBI accession No. X67161 sets forth a complete L1 DNA sequence, as per Longuet et al J. Clin. Microbiol. 34 (3), 738-744 (1996); the HPV 16 complete genome sequence is set forth at NCBI accession No. NC 001526 as per Kennedy et al., J. Virol. 65 (4), 2093-2097 (1991); the HPV 18 complete sequence is set forth at NCBI accession No. NC 001357 as per Cole et al., J. Mol. Biol. 193 (4), 599-608 (1987). Moreover, certain HPV vaccines have been tested in humans. Since vaccines for PV and HPV have been produced, tested, and described elsewhere, a person of ordinary skill, after reading this description, will be able to use the disclosed materials and methods to create vaccines.

One embodiment is a vaccine against diseases caused by papilloma viruses, obtainable by the following method:

(a) One or more expression vectors are injected into mammals. These vectors contain the DNA code for a structural protein of papilloma viruses (PV) or a fragment thereof, whereby in the case of at least some of the expression vectors randomly generated heterologous sequences are inserted into the DNA code.

(b) serums are obtained from the mammals and these are examined for the presence of antibodies against particles of different papilloma virus types.

(c) using the serums examined, the structural protein clones, particularly L1 clones, are identified that code for a polyvalent vaccine and (d) the vaccine is produced from them.

Figure 5:
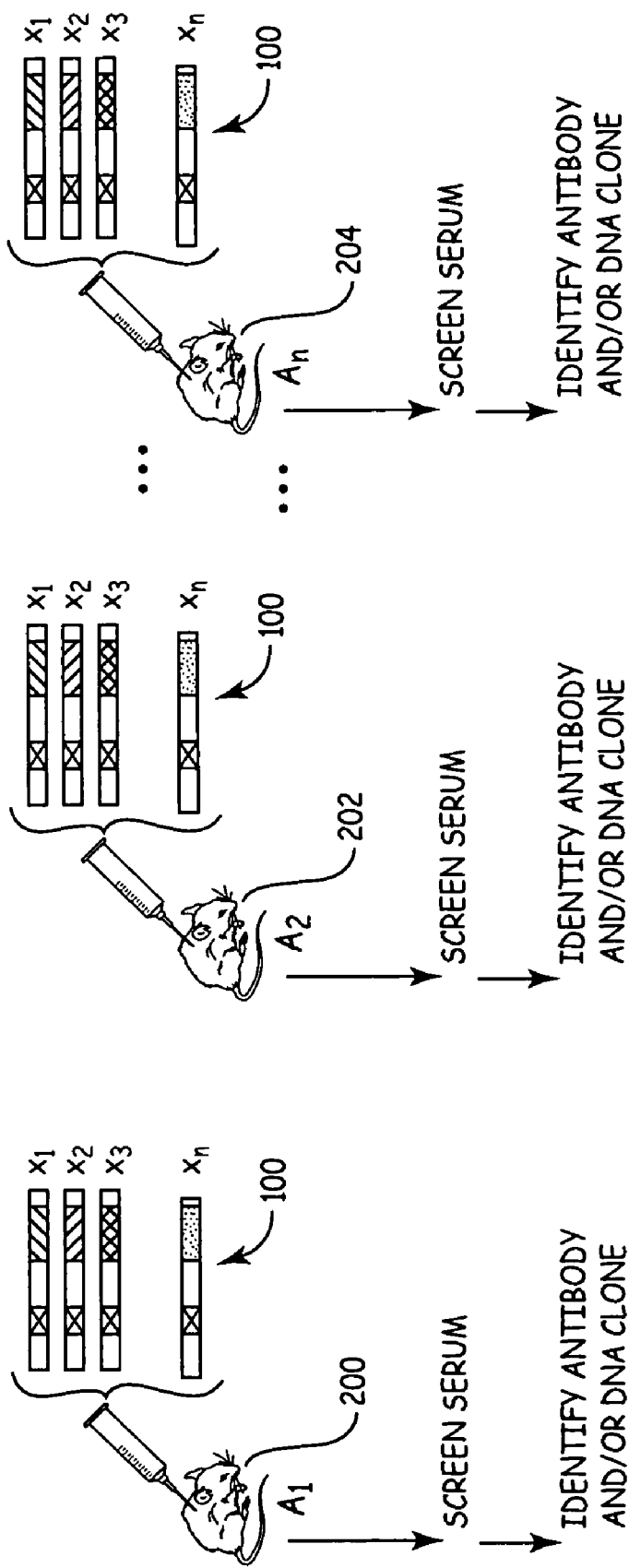
FIG. 5 depicts a combinatorial process for generating an antibody and/or a DNA clone that generates an antibody against a plurality of papilloma virus (PV) types.

Referring to FIG. 5, an embodiment of a method for using a combinatorial process to rapidly screen a large number of nucleic acid clones, e.g., DNA clones, is depicted. Animals A1, A2, A3 . . . . An each receive a portion of library 100 of DNA clones, with the library having members that comprise nucleic acid expression vectors and/or expression cassettes that encode potentially antigenic sequences to elicit an immune response from an animal. The library 100 is divided into a number of groups that corresponds to the number of animal groups An, e.g., x, y, and z for three groups of animals. Each group x, y, z, has a plurality of components, e.g., 1, 2, 3 . . . n components. Each group is injected into a single animal. As shown in FIG. 5, animal (or animal group) A1 receives x1, x2, x3 . . . xn clones of library 100, animal group A2 receives y1, y2 . . . y3 clones of library 100, and An receives z1, z2 . . . z3 clones of library 100. DNA clones in library 100 comprise expression control sequences 300 operably linked to the sequences that are to be expressed in the animal 302, 303, 304, 305, 306, 307, 308, 309, 310, 311, 312, 313. Serum from an animal is screened for the presence of a desired immune response. An antibody and/or a DNA clone encoding an antigen that elicits a desired immunogenic response from an animal is identified.

Library 100 may have a plurality of members that are each a nucleic acid clone that encode potentially antigenic sequences to elicit an immune response from an animal. The clones may encode portions of a PV or HPV virus, e.g., HPV 16, HPV 18, or any other HPV that is known. As described herein, portions of the DNA clones may include randomly generated sequences. The randomly generated sequences may be disposed in or near an known epitope for the HPV. As set forth herein, L1 loop portions include known epitopes for HPVs.

Animals 200, 202, 204 may be any animal that is capable of generating an immune response. For example, animals that have previously been adapted for laboratory uses may be used, including mice, rats, rodents, sheep, cows, calves, goats, dogs, monkeys.

Methods for screening animals for a target molecule having a particular property are known to those of ordinary skill in these arts. ELISA, dot-blot, gel electrophoresis, radiolabeling, immunolabeling, and a plethora of methods for identifying a target molecule are known in the biological sciences. The serum from an animal may be screened for the presence of antibodies by taking advantage of the specific binding of an antibody to a putative target, e.g., to a set of HPV types. Alternatively, other fluids or tissues from the animals may be screened.

The production of antibodies may be accomplished using methods known to artisans of ordinary skill. Polyclonal antibodies may conventionally be obtained from the animal's blood or serum and isolated by weight using a centrifuge and standard purification techniques. Monoclonal antibodies may conventionally be produced using hybridoma cell culture techniques.

The expression "fragments thereof," as used above, indicates that the DNA codes for a protein that is shorter than the wild-type proteins, but which has the characteristics needed for this invention, especially the chemical, physical and/or functional characteristics.

Nucleic acids can be incorporated into vectors. Vectors may be expression vectors containing an expression cassette, which is an inserted nucleic acid segment that is operably linked to an expression control sequence. A vector may be a replicon, e.g., a plasmid, phage, or cosmid, into which another nucleic acid segment may be inserted so as to bring about replication of the inserted segment. An expression vector is a vector that includes one or more expression control sequences, and an expression control sequence is a DNA sequence that controls and regulates the transcription and/or translation of another DNA sequence. Expression control sequences include, for example, promoter sequences, transcriptional enhancer elements, and any other nucleic acid elements required for RNA polymerase binding, initiation, or termination of transcription. With respect to expression control sequences, the term operably linked means that the expression control sequence and the inserted nucleic acid sequence of interest (also referred to herein as the exogenous nucleic acid sequence that is intended to be expressed, also referred to as the exogenous nucleic acid sequence) are positioned such that the inserted sequence is transcribed (e.g., when the vector is introduced into a host cell). A transcriptional unit in a vector may thus comprise an expression control sequence operably linked to an exogenous nucleic acid sequence. For example, a DNA sequence is operably linked to an expression-control sequence, such as a promoter when the expression control sequence controls and regulates the transcription and translation of that DNA sequence. The term operably linked includes having an appropriate start signal (e.g., ATG) in front of the DNA sequence to be expressed and maintaining the correct reading frame to permit expression of the DNA sequence under the control of the expression control sequence to yield production of the desired protein product. Examples of vectors include: plasmids, adenovirus, Adeno-Associated Virus (AAV), Lentivirus (FIV), Retrovirus (MoMLV), and transposons.

There are a variety of promoters that could be used including, e.g., constitutive promoters, tissue-specific promoters, and inducible promoters. Promoters are regulatory signals that bind RNA polymerase in a cell to initiate transcription of a downstream (3'-direction) coding sequence.

Many different types of vectors are known. For example, plasmid vectors and viral vectors, e.g., retroviral vectors, are known. Mammalian plasmid expression vectors typically have an origin of replication, a suitable promoter and optional enhancer, and also any necessary ribosome binding sites, a polyadenylation site, splice donor and acceptor sites, transcriptional termination sequences, and 5' flanking non-transcribed sequences. In addition, the expression vectors preferably contain a gene to provide a phenotypic trait for selection of transformed host cells such as neomycin resistance for eukaryotic cell culture, or tetracycline or ampicillin resistance in *E. coli*. Retroviral vectors, which typically transduce only dividing cells, can be used. Adenoviral vectors, capable of delivering DNA to quiescent cells can be used. Another viral vector system with potential advantages is an adeno-associated viral vector.

As used herein, the term nucleic acid refers to both RNA and DNA, including cDNA, genomic DNA, synthetic (e.g., chemically synthesized) DNA, as well as naturally occurring and chemically modified nucleic acids, e.g., synthetic bases or alternative backbones. A nucleic acid molecule can be double-stranded or single-stranded (i.e., a sense or an antisense single strand). An isolated nucleic acid refers to a nucleic acid that is separated from other nucleic acid bases that are present in a genome, including nucleic acids that normally flank one or both sides of a nucleic acid sequence in a vertebrate genome (e.g., nucleic acids that flank a gene).

The term isolated as used herein with respect to nucleic acids also includes non-naturally-occurring nucleic acid sequences, since such non-naturally-occurring sequences are not found in nature and do not have immediately contiguous sequences in a naturally occurring genome.

An isolated nucleic acid can be, for example, a DNA molecule, provided at least one of the nucleic acid sequences normally found flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid because such sources do not indicate a role for the nucleic acid or its uses. Indeed, there is often no knowledge of the sequences present in such sources until their presence is hypothesized as a result of using hindsight in light of a new sequence.

Examples of delivery of various embodiments as set forth herein, e.g., nucleic acids, vaccines, antibodies, and vectors, include via injection, including intravenously, intramuscularly, or subcutaneously, and in a pharmaceutically acceptable carriers, e.g., in solution and sterile vehicles, such as physiological buffers (e.g., saline solution or glucose serum). The embodiments may also be administered orally or rectally, when they are combined with pharmaceutically acceptable solid or liquid excipients. Embodiments can also be administered externally, for example, in the form of an aerosol with a suitable vehicle suitable for this mode of administration, for example, nasally. Further, delivery through a catheter or other surgical tubing is possible. Alternative routes include tablets, capsules, and the like, nebulizers for liquid formulations, and inhalers for lyophilized or aerosolized agents.

Many known methods for delivering molecules in vivo and in vitro, especially small molecules, nucleic acids or polypeptides, may be used for embodiments described herein. Such methods include microspheres, liposomes, other microparticle vehicles or controlled release formulations placed in certain tissues, including blood. Examples of controlled release carriers include semipermeable polymer matrices in the form of shaped articles, e.g., suppositories, or microcapsules and U.S. Pat. Nos. 5,626,877; 5,891,108; 5,972,027; 6,041,252; 6,071,305, 6,074,673; 6,083,996; 6,086,582; 6,086,912; 6,110,498; 6,126,919; 6,132,765; 6,136,295; 6,142,939; 6,235,312; 6,235,313; 6,245,349; 6,251,079; 6,283,947; 6,283,949; 6,287,792; 6,296,621; 6,309,370; 6,309,375; 6,309,380; 6,309,410; 6,317,629; 6,346,272; 6,350,780; 6,379,382; 6,387,124; 6,387,397 and 6,296,832. Moreover, formulations for administration can include transdermal patches, ointments, lotions, creams, gels, drops, suppositories, sprays, liquids, and powders.

When producing the vaccine according to the invention, the gene coding for PV capsids of a specific type, for example L1, can therefore be modified by inserting randomly generated sequences. Without prior production and cleaning of the capsids, for example by expression of the L1 gene using recombinant vectors such as plasmids, serums are produced through immunization with several L1 expression vectors that can be defined as pools of expression vectors, and these serums are then tested for reactivity with capsids of different PV types. After this, the pools may be isolated, and in this way the capsids with cross-neutralizing epitopes identified.

Persons of ordinary skill in these arts will be able to determine if a nucleotide sequence encodes a given protein or polypeptide, e.g., the L1 protein or a fragment thereof. In general, such determinations typically involve comparison of structural features and sequence identities.

As can be seen from the above detail, a vaccine in accordance with certain embodiments as set forth herein can be either VLPs (virus-like particles) or capsomeres containing modified L1 proteins that may indicate the presence of cross-neutralizing epitopes, in other words which lead to an antibody response directed against various different PV types. Such vaccines can be defined as polyvalent vaccines that can be used against infections with various PV types.

As explained above, DNA-free virus capsids, so-called virus-like particles (VLP), which accumulate in eukaryotic cells after the expression of the main structural protein L1, using recombinant vectors, may be suitable for the induction of neutralizing antibodies. VLPs are empty (free of nucleic acid) virus capsids produced using genetic engineering. Substructures of VLPs, too, known as capsomeres, which result from an incomplete assembly, for example when modified L1 molecules are present, contain neutralizing epitopes, which means they are suitable for producing vaccines in accordance with the invention.

Epitope is another term for antigen determinants. These are areas on the surface of an antigen where a specific antibody binds using its antigen-binding region.

To produce the vaccine according to the invention, a randomly generated heterologous sequence is inserted into a main structural protein, such as the L1 gene, of a specific papilloma virus type, especially into the hyper-variable regions of L1 genes.

The expression "insert" in the sense intended in this invention indicates that the randomly generated heterologous sequences could be present in the structural protein gene in addition to the naturally occurring epitopes, and/or that the naturally occurring epitope in the gene for the structural protein may be exchanged for a randomly generated heterologous sequence.

As an example the production of an L1 gene cassette will be described below, which enables various randomly generated oligo-nucleotides to be inserted into the hyper-variable areas of the L1 structural protein.

For inserting the randomly generated oligo-nucleotides into the DNA sequence of the L1 structural protein, a gene cassette can first be constructed. This gene cassette is characterized by the fact that, for example, the DNA code for the hyper-variable areas of the L1 structural protein is modified such that silent mutations are used to insert monovalent interfaces for restriction endonucleases, where the said interfaces flank these hyper-variable areas. The term 'silent mutation' is one used for the introduction of a modified DNA sequence that carries a recognition point for a specific restriction endonuclease without this changing the amino-acid sequence. The term 'monovalent interface' means a recognition sequence for a restriction endonuclease that occurs only once in the DNA sequence coding for the target protein. For technical reasons this has to be a recognition sequence for a restriction enzyme that may not be present additionally in the plasmids employed for the production of the variable DNA mixtures. The heterologous, randomly degenerated oligo-nucleotides may be constructed in such a way that they are also flanked by the monovalent interfaces, just as they flank the hyper-variable areas of the L1 DNA sequence. This way the gene cassette (in a cloning plasmid) and oligo-nucleotides can be treated with the same corresponding restriction enzymes. Ligation of the oligo-nucleotides into the gene cassette can then occur.

The expression "heterologous sequences", as used in this invention, refers to any sort of DNA sequence that differs from the coding DNA sequence for the naturally occurring epitope in the structural protein in at least one up to a maximum of all nucleotides. This can be achieved by replacing the nucleotides. Because epitopes usually only consist of a few amino-acids that are of the same size range as oligo-proteins, the heterologous sequences can be produced in the customary way, using the DNA sequences of the known epitopes as the basis, for example by oligo-nucleotide synthesis.

For example, if an epitope contains 12 amino acids, the corresponding DNA sequence will consist of 36 nucleotides. For the randomly generated heterologous sequences, one up to a maximum of all of these nucleotides can be substituted. Because one nucleotide can be replaced by a total of three other nucleotides differing from it, when DNA sequences are randomly generated a large number, up to several thousand, of new DNA sequences are created that are heterologous to the original DNA sequence. Because the production of this DNA is not site-specific, such as is the case when for example only one specific nucleotide in a DNA sequence is replaced, it can be defined as a randomly generated DNA sequence A so-called "random library" is an example of a collection of different, heterologous, randomly generated sequences.

Therefore in the case of the randomly generated heterologous DNA sequences employed to manufacture the vaccine in accordance with the invention we find they are ones not produced by site-specific mutations; rather, based on known epitope sequences, at least one nucleotide up to a maximum of all nucleotides are replaced in random fashion by one of the three other conceivable nucleotides, which gives rise to a randomly generated collection of a wide variety of DNA sequences. It is advantageous if the randomly generated heterologous DNA sequence is oriented to the naturally occurring epitopes in respect of the number of nucleotides, or ideally has the same number of nucleotides.

When manufacturing the randomly generated heterologous DNA sequences the DNA sequence of the wild type epitope may be obtained again through the random combining of the nucleotides.

Examples will be given below to show how randomly generated oligo-nucleotides are obtained. Oligo-nucleotides may be produced using the process of oligo-nucleotide synthesis. In this process the nucleotide sequence is produced linearly, in other words the extension of the chain occurs from the reaction of the already present nucleotide sequence with an active pre-stage of the following nucleotide. But to produce degenerated oligo-nucleotides not only the activated pre-stage of a nucleotide can be deployed; the activated pre-stages of 2, 3 or 4 nucleotides can also be introduced. This gives rise to oligo-nucleotide mixtures coding in this position for several different amino acids. If this process is repeated in subsequent stages of the reaction, a combination of different DNA sequences arises. Here both DNA sequences that do not occur in human pathogen PVs result, as well as the sequences that code for the wild-type epitope.

Heterologous sequences are inserted into surface loops of L1 capsids that are hypervariable among papillomaviruses (Chen et al., Mol Cell 5:, 557-567, 2000). As an example, for the main structural protein L1 the sequence area of amino acid 130 to 152 may apply (sequence numbering of HPV16L1 according to Chen et al., Mol Cell 5:, 557-567, 2000). For the 23 amino acids of this sequence section a DNA sequence codes from 69 nucleotides. By also introducing the monovalent sequences, DNA sequences arise with more than 80 nucleotides. Alternatively the area of amino acids 260-299 or amino acids 349-360 may be selected. With complementary primers, different replenishing reactions with DNA polymerases can be used to synthesize the matching strand. Thus, for example, between 3 and 200 nucleic acids may be introduced as random sequences; values outside of this explicitly range are contemplated, as well as all values and ranges within the explicitly stated range, e.g, between 6 and 200, at least 3 or 6, less than 300, and between 12 and 150. The double-stranded DNA obtained this way can then be modified directly with the corresponding restriction endonucleases and ligated into the L1 gene cassette. To obtain greater efficiency the specialist may firstly ligate the double-stranded DNA sequences, using 'blunt end' clonings, into cloning vectors. From these 'random libraries' the DNA sequences can then be re-cloned with a high degree of efficiency into the L1 gene cassettes.

The randomly generated heterologous DNA sequences are then, as described above, inserted into the gene of the structural proteins of the PV, and in particular into the L1 gene of papilloma viruses of a specific type. HPV, BPV and CRPV are representative types of papilloma viruses. Particularly, insertion into the hyper-variable regions of L1 genes is carried out. The invention has been described here using the preferred structural protein gene L1, but it is not limited to this.

The length of the inserted heterologous DNA, in other words the number of nucleotides, is guided, as described above, by the length of the naturally occurring epitope. It is selected with particular care being taken not to interfere with the formation of the capsomeres and VLPs. Persons of ordinary skill in these arts may use publicly accessible information to identify suitable epitopes of PVs and HPVs. For example, information about HPV epitopes is set forth in Vaccine 2003, 21(19-20):2506-15; Intervirology. 2002, 45(1):24-32; Eur J Immunol. 2000, 30:2281-9; and Biol Chem. 1999, 380:335-40.

If the original epitopes of the L1 gene are replaced by the randomly generated heterologous DNA sequences, it may be that only one of the epitopes is replaced. However several, even all of the maximum possible epitopes in the L1 gene may be replaced by randomly generated heterologous sequences.

The L1 gene into which the randomly generated heterologous sequences are inserted may subsequently be cloned into eukaryotic expression vectors. In this case many bacterial clones may arise, and from this large number of bacteria clones sub-groups can then be formed. In other words this large number of bacteria clones is split up into pools of a few thousand bacteria clones and deployed for the production of vaccines in accordance with the invention.

To produce the vaccine in accordance with the invention one or more than one expression vector(s) are injected into mammals, whereby these vectors can be characterized as described above. The term 'more than one' here indicates that a pool of expression vectors can be used, containing up to 10,000, but particularly up to 5,000 expression vectors that differ from each other. The differences in the expression vectors then exist in particular in the randomly generated heterologous DNA cloned into them. As is clear from the above comments on randomly generated heterologous DNA, the expression vectors may also contain DNA sequences that were obtained when randomly generating the DNA sequences, but which—because the generation is also random in this case—are identical with the DNA sequence for the wild-type epitope. Consequently expression vectors are injected into the mammals where at least some, up to a maximum of all, of them contain randomly generated heterologous DNA sequences inserted into the DNA code.

These preselected pools are used for a DNA vaccination (genetic immunization). This consists of a recognized immunization procedure in which, unlike conventional immunizations, no antigens are injected; instead the DNA code is injected into a corresponding expression vector. The intramuscular application form has been shown to be favorable for DNA vaccination, because obviously in this case absorption and expression of the gene by the cell takes place before the DNA is broken down. The immune reaction then takes place in response to the expressed protein.

One advantage of DNA vaccination can be seen particularly in the fact that the virus particles no longer need to be manufactured and purified, for example by expression of the L1 gene using recombinant vectors. Thus DNA vaccination can be carried out simply and rapidly.

This DNA vaccination may be carried out on mammals such as rats, mice, hamsters and guinea pigs.

Serums can then be obtained from the test animals in the normal way, which are tested for reactivity with different types of papilloma virus. Testing can be done using ELISA, which are specific for papilloma virus types.

The DNA pools deployed for the DNA vaccination that provoke an immune reaction against different papilloma virus types can subsequently be isolated and again analyzed using DNA. In this way clones can be identified that code for VLPs or capsomeres and which contain cross-neutralizing epitopes. These are epitopes that lead to an antibody reaction against various papilloma virus types.

After this the corresponding DNA clones can be further examined using the customary procedures of genetic engineering, and, as the case may be, the corresponding virus particles produced, isolated and purified. Additionally L1 molecules, for example, can be expressed, VLPs or capsomeres can be produced and the immunity of the purified particles can be examined. Finally it is possible in this way to obtain the vaccine according to the invention, which is characterized by the fact that immunization against more than one papilloma virus type is possible. The vaccine according to the invention is, therefore, a multivalent vaccine that induces immune protection against diseases caused by different PV types.

In a preferred embodiment of the vaccine according to the invention the papilloma virus is a human pathogenic papilloma virus. This makes it possible to treat diseases caused by human pathogenic papilloma viruses with the vaccine according to the invention.

In another preferred embodiment the structural protein is L1, because this is particularly well suited for producing the vaccine according to the invention.

In another preferred embodiment the structural protein creates DNA-free virus capsids or capsomeres.

The object of this invention is also a DNA vaccine comprising one or more expression vector(s) containing the DNA code for a structural protein of papilloma viruses or a fragment thereof, wherein in at least some of the expression vectors randomly generated heterologous sequences are inserted into the DNA code.

As regards the structures and manufacture of the DNA vaccine reference should be made to the descriptions given above.

When administering the DNA vaccine according to the invention, the structural protein gene is expressed and immunization is carried out against the expressed protein. In this way immunization is achieved with particular ease.

An embodiment for manufacture a vaccine is a process wherein (a) One or more expression vectors are introduced into mammals. These vectors encode at least a portion of a structural protein of a papilloma virus (PV), and the expression vectors may further encode at least one randomly generated heterologous nucleic acid sequence, (b) sera are obtained from the mammals, and examined for the presence of at least one polyvalent antibody that recognizes a plurality of papilloma virus types, (c) using the sera, the portions of the expression vectors that encode epitopes(s) that cause the presence of the at least one polyvalent antibody are identified, and (d) a vaccine is produced from the expression vectors(s) and/or encoded epitopes thus identified.

The individual steps of the procedure according to the invention have already been described in connection with the vaccine according to the invention, so reference is made to the respective embodiments.

The procedure according to the invention is characterized by the fact that the modified genes of the structural protein (insertion of randomly generated heterologous DNA) no longer have to be tested individually before immunization for their capacity to form VLPs or capsomeres. Instead, pools of recombinant DNA expression vectors are used to immunize mammals, in particular mice. The serums obtained are tested for the presence of antibodies against particles of various papilloma virus types, especially HPV types. If the reaction is positive, in other words if cross-neutralizing epitopes can be demonstrated, the pools of expression vectors are isolated and the corresponding proteins analyzed.

This procedure according to the invention enables the testing of a large number of variants of papilloma virus particles, especially capsids, for their immunogenic qualities, without having to express and purify the particles individually by expression of the mutated structural protein beforehand. Moreover, the procedure according to the invention enables the production of highly effective, multivalent papilloma virus vaccines quickly, simply and at a low cost.

The vaccine according to the invention is best suited as a polyvalent vaccine used in vaccinations against diseases caused by papilloma viruses, particularly diseases that are caused by more than one kind of papilloma virus. Examples of these diseases are warts, papillomas, acanthomas, and skin and cervical cancers.

Further examples are provided below. These examples demonstrate that DNA immunization of animals with a plurality of DNA clones created measurable amounts of antibodies for each clone. Moreover, different clones may be introduced at ratios of more than 100:1 so that animal sera having antibodies for multiple clones can be readily screened. In fact, ELISA screening techniques were used in the Examples, demonstrating that the proposed methods are compatible with high-throughput screening systems. Thus, large libraries can be effectively analyzed. These examples also demonstrate that DNA immunization is effective to produce anti-HPV antibodies. Moreover, the anti-HPV antibodies were generated after mice were exposed to a plurality of vectors presented at a variety of ratios relative to each other. As shown in FIGS. 1-4, anti-HPV 16 L1 antibodies were induced in response to a small amount of HPV 16 L1 DNA, even in the presence of other DNA vectors.

These data show that over one hundred DNA clones may be introduced into a mouse to generate antibodies against the antigens for which the DNA clones code. The total amount of DNA introduced into the mice tested as shown in FIGS. 1-4 was kept constant. As shown in FIG. 4, the HPV 16 and HPV 18 clones were effective at 100:1 ratios and at 1:100 ratios. Therefore other clones that generate antigens for other types of HPV can also be expected to be effective at about the same dosage ranges. Since a plurality of clones are effective at the minimum dose, a multiplicity of clones should be effective at the same dose. Moreover, if about 100 clones are introduced at the minimum dose, then the total amount of DNA thereby introduced into an animal would be about the same as what was tested in the Examples. Therefore a single mouse can be inoculated with at least one hundred clones and be expected to produce detectable amounts of antibodies against each clone. Furthermore, all of the dosage ranges that were tested and reported herein were found to be effective so that higher ratios can reasonably be expected, and the successful use of more than 100 clones in a single animal may reasonably be expected.

EXAMPLE 1

As shown in FIG. 1, mice immunized with various ratios of HPV 16 L1 DNA and an empty pUF3 vector were positive at all tested ratios for antibodies against HPV 16 L1.

DNA of HPV 16 L1 (L1 was cloned into a suitable expression vector) was mixed in different ratios with other expression constructs (as indicated in Figures) keeping the total amount of DNA constant. The following ratios were used: 50/0;25/25; 10/40; 5/45; 2.5/47.5; 0.5/49.5; 0/50 (HPV16 L1/other vectors as indicated). Mice were then immunized three times with 50 µg each time using the ratios above. Sera were collected and tested in ELISA for antibodies against HPV 16 and 18 L1 virus-like particles (produced in baculovirus-infected insect cells). The following immunization protocol was used: day 0, 100 µl Cardiotixin i.m., prebleed; day 5, 50 µg DNA mixture in 100 µl PBS; day 19, 50 µg DNA mixture in 100 µl phosphate buffered saline; day 38, 50 µg DNA mixture in 100 µl PBS; day 48, final bleed. Three mice in each group, mice were C57/b16 strain. The following ELISA was used: Microtiter plates were coated with 0.17 µg of VLPs per well. After blocking with skim milk, plates were incubated with antisera (1:25 in skim milk) for 1 hr. Antibodies were detected with goat-anti-mouse IgG horseradish peroxidase conjugates. After staining, absorption was measured after 20 min. in a Titertech automated plate reader at 405 nm wavelength.

EXAMPLE 2

Figure 2:
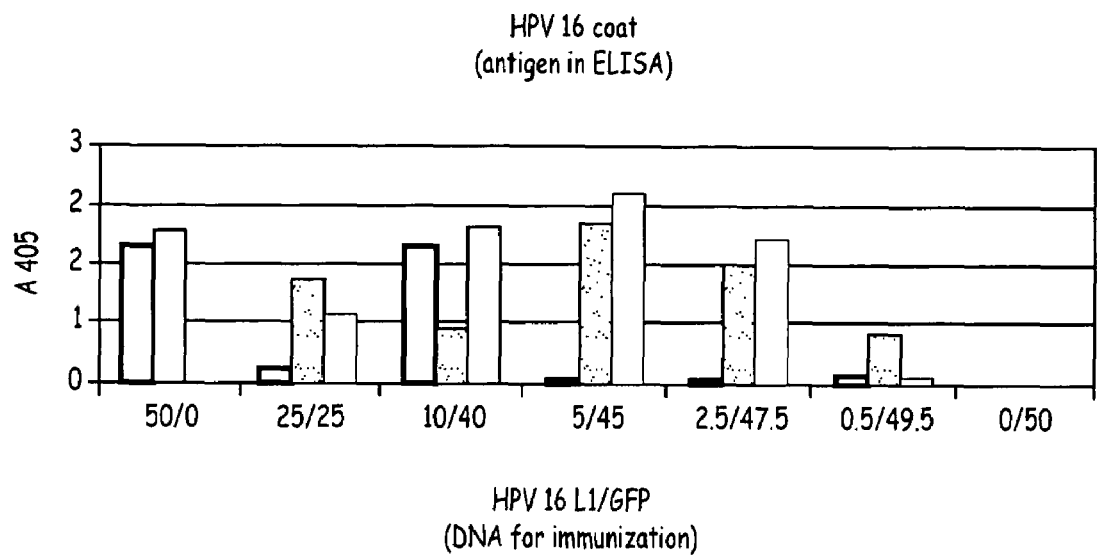
FIG. 2 is a plot of experimental data wherein mice (three per group) were immunized with different amount ratios of HPV 16 L1 and GFP DNA. The sera of the mice were tested in VLP-based ELISA for the presence of anti-HPV 16 antibodies.

As shown in FIG. 2, mice immunized with various ratios of HPV 16 L1 DNA and a DNA vector for GFP were positive at all tested ratios for antibodies against HPV 16 L1. Materials and methods as set forth in Example 1 were followed, unless otherwise indicated.

EXAMPLE 3

Figure 3:
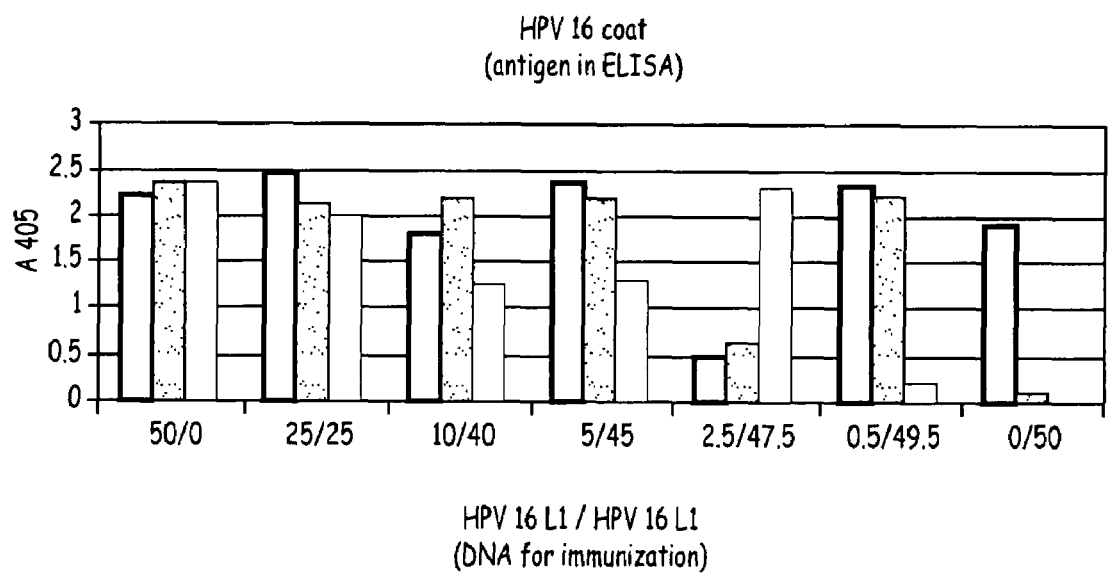
FIG. 3 is a plot of experimental data wherein mice (three per group) were immunized with different amount ratios of HPV 16 L1 DNA and HPV 18 L1 DNA. The sera of the mice were tested in VLP-based ELISA for the presence of anti-HPV 16 antibodies.
Figure 4:
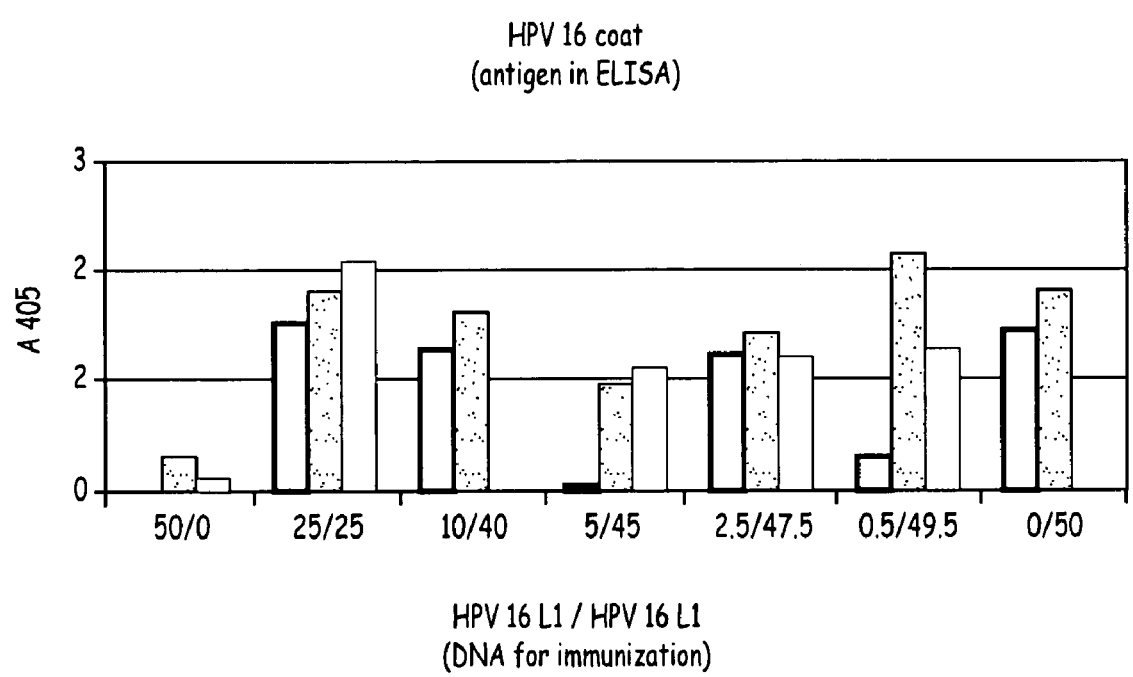
FIG. 4 is a plot of experimental data wherein mice (three per group) were immunized with different amount ratios of HPV 16 L1 and HPV 18 L1 DNA. The sera of were tested in VLP-based ELISA for the presence of anti-HPV 18 antibodies.

As shown in FIGS. 3 and 4, mice immunized with various ratios of HPV 16 L1 DNA HPV 18 L1 DNA were positive at all tested ratios for antibodies against HPV 16 L1 and HPV 18 L1. Materials and methods as set forth in Example 1 were followed, unless otherwise indicated.

All patents, patent applications, and publications referenced herein are hereby incorporated by reference herein.

The invention claimed is:

1. A method of making an antibody against a plurality of papilloma virus types, comprising:

introducing into a mammal a plurality of DNA clones from a plurality of HPV types, wherein each clone of said plurality of DNA clones comprises an expression vector comprising DNA that encodes at least a portion of a L1 structural protein of a human papilloma virus comprising the coding sequence of at least one naturally occurring epitope of said papilloma virus or at least one randomly generated heterologous sequence which is derived from the coding sequence of a naturally occurring epitope by the exchange of one or more nucleotides;

testing the mammal to detect antibodies against a plurality of papilloma virus types generated by introducing the plurality of DNA clones into the mammal; and harvesting antibodies from the mammal.

2. The method of claim 1 wherein at least a portion of a structural protein of a papilloma virus comprises at least one randomly generated heterologous sequence which is derived from the coding sequence of a naturally occurring epitope by the exchange of one or more nucleotides.

3. The method of claim 2 wherein the DNA clone heterologous sequences have a length of between 6 and 200 bases.

4. The method of claim 2 wherein the DNA clones comprise DNA that encodes for a hyper-variable portion of the L1 protein, and wherein the at least one randomly generated heterologous sequence comprises a heterologous sequence inserted into the hyper-variable portion of the L1 protein.

5. The method of claim 2, wherein the least one randomly generated sequence is disposed in a surface loop of the L1 structural protein.

6. The method of claim 1, wherein the number of DNA clones is between 10 and 10,000.

7. The method of claim 1, wherein the number of DNA clones is at least 25.

* * * * *